United States Patent [19]  [11] 4,290,943
Birr  [45] Sep. 22, 1981

[54] METHOD OF PREPARING POLYPEPTIDES

[75] Inventor: Christian Birr, Leimen, Fed. Rep. of Germany

[73] Assignee: Max-Plank-Gesellschaft, Gottingen, Fed. Rep. of Germany

[21] Appl. No.: 39,979

[22] Filed: May 17, 1979

[30] Foreign Application Priority Data

Jul. 11, 1978 [DE] Fed. Rep. of Germany ....... 2830442

[51] Int. Cl.³ .................... C07C 103/52; C08L 37/00
[52] U.S. Cl. ................................ 260/112.5 R; 260/8
[58] Field of Search ................ 260/112.5 R, 112.5 S, 260/8

[56] References Cited

U.S. PATENT DOCUMENTS

| 3,715,190 | 2/1973 | Park et al. | 260/112.5 R |
| 3,994,871 | 11/1976 | Kamber et al. | 260/112.5 R |
| 4,028,315 | 6/1977 | Bodanszky et al. | 260/112.5 R |
| 4,062,746 | 12/1977 | Rick et al. | 260/112.5 R |
| 4,093,609 | 6/1978 | Sarantakis | 260/112.5 S |

OTHER PUBLICATIONS

Takahashi, Bull. Chem. Soc. Japan 50 (12) 3344–3348 (1977).
T. Mizoguchi, et al., Chem. Pharm. Bull. 18, (1970) 1465–1474.

Primary Examiner—Delbert R. Phillips

[57] ABSTRACT

The present invention relates to a method for the preparation of polypeptides by the stepwise condensation of amino acids on a solid support material, which material comprises condensing, as a starting material, amino acids having an N-terminal of α,α-dimethyl-3,5-dimethoxybenzyloxycarbonyl, or peptide fragments which are N-terminally protected, utilizing as the support material a slightly cross-linked carrier material activated with bromoacetyl bromide with the formation of bromoacetyl phenyl groups, splitting off, in the course of the synthesis, the peptide fragments formed, separating same from contaminating by-products, and binding them again to the support material.

4 Claims, 1 Drawing Figure

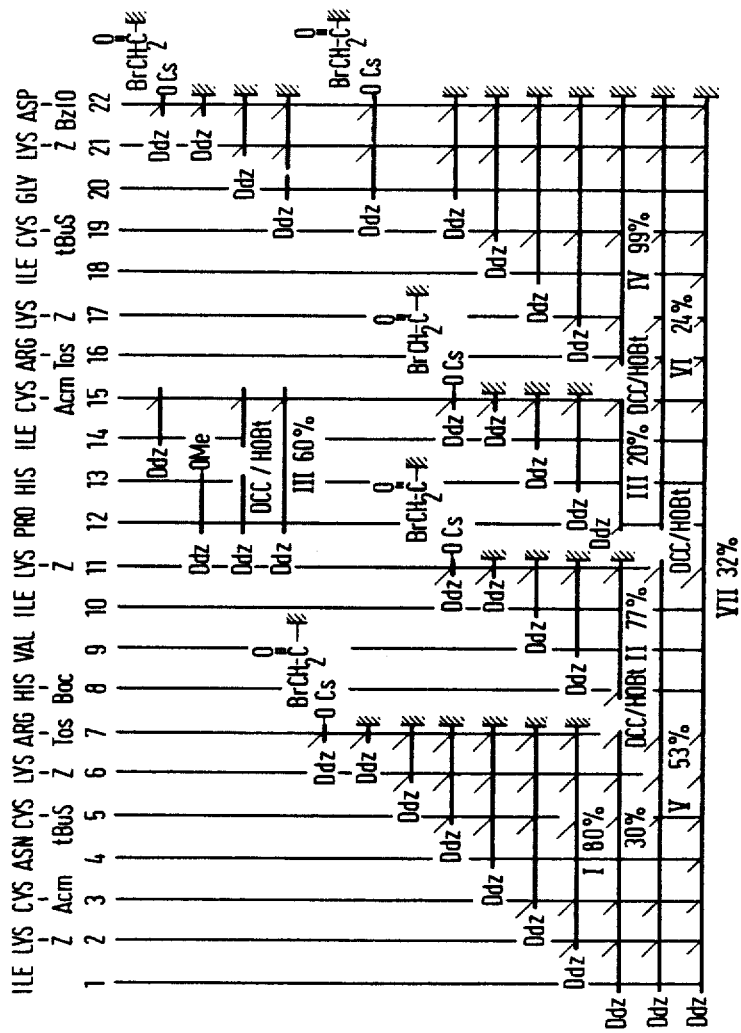

METHOD OF PREPARING POLYPEPTIDES

The invention relates to a method of preparing polypeptides. More specifically, the invention provides a process for preparing the peptide MCD, which degranulates mast cells and has anti-inflammatory activity.

BACKGROUND

It has long been known to form peptides by the step-by-step combining of amino acids in solution. However, the solid-phase peptide synthesis described in 1962 by Merrifield (Fed. Proc., Fed. Amer. Soc. Exp. Biol. 21 [1962] 412) has proven to be substantially more successful; in this method, the condensation of the individual amino acids is performed on a solid support material (preferably slightly cross-linked polystyrene), until finally the finished polypeptide is split off from the support. The advantage of the Merrifield synthesis is that it is performed in heterogeneous phase, so that it becomes easily possible to separate the reagents used in the peptide synthesis from the actual synthesis product bound to the support material. The disadvantage of the Merrifield synthesis is that the chemical reactions used for the sequential synthesis are not, of course, quantitative, so that to some extent the reaction does not take place as desired, and therefore contaminating peptides are simultaneously synthesized and can be separated only with extraordinary difficulty. Particularly in the case of the longer amino acid sequences of 50 and more amino acids, even if the individual steps are 99% effective, the multiplicity of the reactions results in an immense number of by-products in addition to the targeted peptide, which may have either excessively short amino acid chains or may have defects in the amino acid sequence.

Therefore, there has been a need for improving the fundamentally simple Merrifield synthesis so as to make it possible to form peptides of even higher molecular weight having a great number of amino acids in the chain, and containing little or no undesired by-products.

THE INVENTION

It has now been found that it is possible to prepare polypeptides by the step-by-step condensation of amino acids by the Merrifield solid phase technique, and to do so in a simple manner and achieve high purity while avoiding the formation of by-products. In the invention there is used a support material that has been activated in a certain manner, and peptide fragments or amino acids protected at the N-terminus by a certain protective group. Sub-fragments of the ultimate peptide are built up on the support material, then cleaved off, purified and bound again to the support material, and then combined with one or more additional sub-fragments of the end product peptide.

Accordingly, the process of the invention for preparing polypeptides comprises step-by-step condensation, in the desired sequence, of amino acids having protective groups if necessary, on a solid support material containing phenyl groups. The improvement of the present invention comprises the use of a slightly cross-linked support material activated with bromoacetyl bromide, with the formation of bromoacetylphenyl groups, using amino acids having an N-terminal α,α-dimethyl-3,5-dimethoxybenzyloxycarbonyl group or using peptide fragments protected appropriately at the N-terminus, splitting the peptide fragments from the support material in the course of the synthesis, separating them from contaminating by-products, and binding them again to the support material for further synthesis.

In the method of the invention, the amino acids or peptide fragments are bound to the support material by the bromoacetyl groups present on the support material, thereby achieving a relatively easily releasable bond which can be cleaved by the action of acid reagents and especially basic reagents, for example by the use of trifluoroacetic acid and hydrogen bromide in organic solvents, or by the use of liquid hydrogen fluoride, or by basic hydrolysis, by hydrazinolysis, or especially, and preferably, by ammonolysis.

With the aid of this easily cleavable bond to the support material it becomes possible to split the formed peptide fragments from the support while sparing any protective groups that might be present, to remove impurities, to perform analyses, and to bind the individual peptide fragments again to the support material and build them up further or to unite them to form the desired peptide. At the same time it has been found to be especially advantageous to introduce, as the N-terminal protective group for the amino acids or peptide fragments, the α,α-dimethyl-3,5-dimethoxybenzyloxycarbonyl group, which can easily be detected, as such and in the form of its cleavage products, by optical methods, so that it is thus possible to follow the progress of and control the synthesis of the peptides by simple photometric methods.

Since in the binding of the initial amino acids to the activated support material containing bromoacetylphenyl groups undesirable secondary reactions can occur, such as a cycloazomethine formation of the C-terminal residue or a splitting off of diketopiperazine, pursuant to a preferred embodiment of the method of the invention, either peptide fragments composed of at least three amino acids or, as the initial amino acid, isoleucine, leucine, valine or the amino acids cysteine and lysine protected at the mercapto group or amino group, with which these secondary reactions cannot occur, are bound to the activated support material.

In another preferred embodiment of the invention, a number of different peptide fragments of the desired polypeptide are prepared independently of one another and split off from the support material, and then, after separation of contaminating byproducts and reagents, two peptide fragments adjacent one another in the desired sequence are condensed, and at least one of these fragments is bound again to the support material in the manner described above, prior to performing the condensation whereby the desired end-product peptide is formed.

Pursuant to another preferred embodiment of the invention, the method is directed to the preparation of the pharmacologically extremely interesting peptide MCD of the following formula:

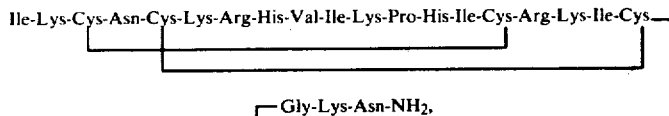

which is characterized in that first the peptide fragments I (Ddz-Ile-Lys[Z]-Cys[Acm]-Asn-Cys[Stbu]-Lys[Z]-Arg[Tos]), II [Ddz-His[Boc]-Val-Ile-Lys[Z]), III (Ddz-Pro-His-Ile-Cys[Acm]) and IV (Ddz-Arg[Tos]-Lys[Z]-Ile-Cys[StBu]-Gly-Lys[Z]-Asp[OBzl]) are formed, fragments I and II and fragments III and IV are united to fragments V (Ddz-Ile-Lys[Z]-Cys[Acm]-AsnCys[StBu]-Lys[Z]-Ars[Tos]-His[Boc]-Val-Ile-Lys[Z]) and VI (Ddz-Pro-His-Ile-Cys[Acm]-Ars[Tos]-Lys[Z]-Ile-Cys[StBu]-GlyLys[Z]-Asp[OBzl]), and finally the fragments V and VI are combined with peptide VII (Ddz-Ile-Lys[Z]-Cys-[Acm]-AsnCys[StBu]-Lys[Z]-Arg[Tos]-His[Boc]-Val-Ile-Lys[Z]-Pro-HisIle-Cys[Acm]-Arg[Tos]-Lys[Z]-Ile-Cys[StBu]-Gly-Lys[Z]Asp[OBzl]), peptide VII is split off from the support, and in a known manner the protective groups are split off and the $Cys^5$-$Cys^{19}$ and $Cys^3$-$Cys^{15}$ disulfide bridges are formed.

In the method of the invention, the support material is a slightly crosslinked and hence insoluble but swelling support material containing phenyl groups, especially a polystyrene gel which has been crosslinked with less than 0.5% of divinylbenzene. This support material is activated by reaction with bromoacetyl bromide, whereby bromoacetyl groups are introduced into the polystyrene gel. These functional groups permit easy binding of the amino acids or peptide fragments required for the building of the peptide, by means of the corresponding C-terminus. The carboxylate group of the amino acid or peptide fragment reacts with the splitting off of bromide, and forms an ester group on the acetophenyl group of the polymeric support, which can easily be cleaved again under basic conditions. At the same time, depending on the group desired on the split-off peptide fragment, a number of basic methods known in peptide chemistry can be applied, such as for example hydrolysis if carboxyl groups are to be formed, hydrazinolysis if hydrazine groups are to be formed which can be transformed to azide groups, and cleavage with ammonia with the formation of amide groups. Ammonolysis is performed preferably by using as the cleavage reagent an organic solvent saturated with ammonia, especially dioxane. However, it is also possible to use to advantage a mixture of dimethylformamide and methanol (4:1 by volume) saturated with ammonia at 0° C., or a 10% solution of ammonia in a mixture of dioxane and methanonol (9:1 by volume).

The support material used in accordance with the invention possesses the properties necessary for the desired solid phase synthesis, namely the necessary insolubility in the solvents used, a mechanical stability and a sufficient chemical inertness towards the reagents involved. The support material is preferably in the form of small globules having a diameter of preferably 0.1 to 0.2 mm.

On account of the mechanical delicacy of these support globules, it is preferable to operate in a centrifugal reactor in which the gel globules are held against a porous wall of the rotor under the action of the centrifugal force produced by the rotation, and at the same time the liquid reagents flow through them, so that a largely quantitative reaction can be achieved in the individual steps.

The amino acids or peptide fragments used in accordance with the invention are protected at the N-terminus by the α,α-dimethyl-3,5-dimethoxy-benzyloxycarbonyl group (Ddz protective group) which is substantially more acid-labile than the tert.-butyloxycarbonyl group (Boc protective group) so frequently used in peptide chemistry. This protective group and amino acids provided with them have already been described in Peptides (1972), pp. 72–77. Amino acids protected with this group are stable against auto-acidolysis in solid form and in the form of solutions, and they are prepared by reacting the amino acids with the hydazide or azide derivative of the protective group compound.

The great advantage of this protective group used in accordance with the invention is to be seen in the fact that it can relatively easily be split off under acid conditions, for example by the use of trifluoracetic acid or hydrochloric acid in organic solvents such as dichloromethane, chloroform, dimethylsulfoxide and mixtures thereof. It is preferable to use an 0.5 to 10% solution of trifluoracetic acid in dry dichloromethane. When this cleavage reagent is used, the protective group is completely split off in the course of 5 to 30 minutes at 20° C., depending on the chosen dilution of the trifluoracetic acid. Preferably the Ddz protective group is split off from support-bound Ddz peptides with 5% trifluoracetic acid in the course of 15 minutes, and from Ddz peptides in solution in the course of about 8 minutes.

An additional advantage is to be seen in the fact that the protective group as well as the cleavage products formed from it, namely 3,5-dimethoxy-α-methylstyrene and 3,5-dimethoxyphenyldimethylcarbinol show characteristic ultraviolet bands at 230 and 280 nm, which make it possible to control and supervise the course of the synthesis by photometric methods, by circulating the reaction solutions through the above-mentioned centrifugal reactor and an ultraviolet spectrophotometer, which makes it possible constantly to follow and supervise the course of the reaction by means of the ultraviolet bands of the protective groups or their cleavage products. Thus it is easy to determine when the reaction of the last amino acid added or the last peptide fragment introduced has been substantially completed.

In the practice of the method of the invention, a polystyrene crosslinked with less than 0.5% of divinylbenzene is preferably used as the support material. It is activated by providing it with bromoacetylphenyl groups by reaction with bromoacetyl bromide in nitrobenzene. This bromoacetylation can be catalyzed by aluminum chloride and performed at room temperature by reaction for a period of 20 hours, whereby a support material is obtained having 0.05 to 5 and preferably 0.5 to 1.1 milliequivalents of reactive bromoacetylphenyl groups per gram.

Then the amino acids or peptide fragments protected at the terminal amino acid with the α,α-dimethyl-3,5-dimethoxybenzyloxycarbonyl group are bound to the support material activated in the described manner, this being accomplished preferably by introducing the protected amino acids or peptide fragments by means of the corresponding caesium salts of the carboxyl groups. The lipophilic caesium salts of the amino acids or peptide fragments in dimethylformamide are used in a slight excess, for the purpose of avoiding base-catalyzed racemization and secondary reactions. With a caesium salt excess of only 50%, one achieves a complete reaction of the bromoacetyl groups present in the support material with not only the amino acids protected at the N-terminus, but also with dipeptides and tripeptides, under identical conditions. For the introduction of the amino acids or peptide fragments into the support material it is possible to use tetra-alkylammonium salts instead of caesium salts, because these quaternary cations also have a lipophilic character. In any case, a complete transformation of the bromoacetylphenyl groups of the support material can be accomplished in this manner.

After the usual washing out of the reactants and impurities, the N-terminal protective $\alpha,\alpha$-dimethyl-3,5-dimethoxybenzyloxycarbonyl groups are split off by acidolysis, preferably through reaction with a 5% solution of trifluoroacetic acid in dichloromethane. After the support material has been washed, a deprotonization is performed on the proton-blocked terminal amino groups by reaction with tertiary amines such as triethylamine, diisopropyl-ethyl amine or N-methylmorpholine, in organic solvents, such as dichloromethane, chloroform or dimethylformamide. After the necessary washing, the next amino acid or the next peptide fragment protected at the N-terminus is coupled on with the formation of a peptide bond. This peptide bond is achieved in a known manner, for example by activation with dicyclohexylcarbodiimide, by using symmetrical or mixed amino acid anhydrides, by using active esters, or by redox condensation. Then, after the support material has been washed free of reagents, the next amino acid of the desired sequence or another peptide fragment is added on in the manner stated, until finally a peptide fragment of sufficient size is present on the support material.

In accordance with the invention, the peptide fragments formed are cleaved off from the support material in the course of the synthesis, this being accomplished by means of the cleavage reagents specified above, and especially by basic hydrolysis, preferably by ammonolysis. After the removal of impurities, such as byproducts and reagents, the pure peptide fragments obtained are again, preferably in the form of the caesium salts, bound to fresh support material having bromoacetylphenyl groups, and then additional amino acids or peptide fragments protected at the N-terminus by $\alpha,\alpha$-dimethyl-3,5-dimethoxybenzyloxycarbonyl protective groups are added on by condensation, until the desired endproduct peptide is present on the support material, from which it is split off, then isolated and purified in the conventional manner.

In this manner it is possible, especially by an intermediate cleaving off of the peptide fragments, purifying these peptide fragments and combining them in the desired sequence, to synthesize the desired peptide end products substantially free of such byproducts as shorter-chain peptides or peptides of incorrect sequence. This is accomplished by the method of the invention in that the peptide fragments formed can easily be cleaved away from the support material, especially without splitting off the protective groups present, and can be freed of impurities even in the intermediate steps of the synthesis, and because, lastly, on account of the special protective group used in accordance with the invention, namely the $\alpha,\alpha$-dimethyl-3,5-dimethoxybenzyloxycarbonyl group, a constant photometric supervision of the course of the reaction is assured, so that a virtually quantitative reaction can be achieved in the individual condensation stages.

The invention will be further explained hereinbelow in connection with the preferred procedure for the preparation of the mast cell degranulating peptide MCD, which is known to be a component of bee venom. The fully protected sequence of the MCD peptide has also been synthesized by the inventor and coworkers in solution in a conventional manner. This very basic bee venom component is of especial interest, since it can be used pharmacologically in combatting rheumatic diseases, so that its synthetic preparation is highly desirable.

This synthesis of the MCD peptide will be further explained in conjunction with the appended drawing which is a diagrammatic representation of how the peptide MCD is built up of individual peptide fragments.

The peptide MCD corresponds to the general formula:

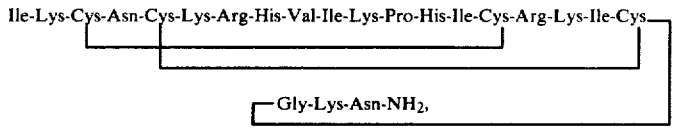

and it is obtained by the use of the method of the invention by first synthesizing the above-specified peptide fragments I, II, III and IV, then uniting fragments I and II to V and III and IV to VI, then combining fragments V and VI in the manner of the invention to form fragment VII, cleaving the protected MCD peptide (VII) from the support, removing its protective groups in a known manner, and forming the two disulfide bridges in the conventional manner.

For this purpose, the amino acids protected at the N-terminus with $\alpha,\alpha$-dimethyl-3,5-dimethoxybenzyloxycarbonyl groups (Ddz groups) are applied in the form of their caesium salts to the polystyrene which has been crosslinked with less than 0.5% of divinylbenzene and has from 0.5 to 1.1 milliequivalents of bromoacetylphenyl groups per gram. At the same time, the caesium salts of the amino acids or of the protected peptide fragments, preferably protected tripeptides, are placed in dimethylformamide, and a complete reaction of the bromoacetylphenyl groups is achieved in the course of three days at 40° C. These caesium salts are used preferably in a 1.5-fold excess.

The condensation of the peptide bond is performed with the use of dicyclohexylcarbodiimide, which together with the N-terminally protected amino acid which is to be bound, is used in a three-fold to five-fold excess. If, instead, N-terminally protected peptide fragments are attached by condensation, a six- to ten-fold excess of 1-hydroxybenzotriazole (HOBt) must additionally be added to suppress racemization. The derivatives obtained are washed with dichloromethane and a 4:1 mixture of dichloromethane and methanol. All of the reactions, including the splitting off of the protected peptide fragments or peptides from the support material, which can be performed in a 1:3 mixture of methanol and dioxane in addition to the method specified on page 8, line 21, are performed in a centrifugal reactor under constant photometric observation of the reaction liquids on the basis of the above-specified ultraviolet bands produced by the protective group or its cleavage products.

First the peptide fragment I (Ddz-Ile-Lys[Z]-Cys-[Acm]-Asn-Cys[StBu]-Lys[Z]-Arg[Tos]), which contains the amino acids 1 to 7, is formed with a yield of 82%. After this peptide fragment has been split off from the support material it is purified by gel chromatography (Sephadex LH 20 with a dioxane-methanol mixture (1:1) and on silica gel with a trichloromethane-methanol gradient). The material is obtained with a yield of 34% with respect to the amino acids initially applied to the support material. The amino acid analysis of the heptapeptide is in agreement with the theory.

Then peptide fragment II (Ddz-His[Boc]-Val-Ile-Lys[Z]), which includes amino acids 8 to 11, is formed with a yield of 77% on the support material, where it is linked to peptide fragment I, which was used in an excess, using for this purpose dicyclohexylcarbodiimide 1-hydroxybenzotriazole in dimethylformamide. After three days, photometric inspection of the reagent solution reveals the complete condensation of peptide fragment I. Then peptide fragment V is cleaved off with benzyltrimethylammonium hydroxide in a 1:3 mixture of methanol and dioxane, and is purified over silica gel by means of a trichloromethane-methanol gradient. The peptide fragment is obtained in a yield of 53% (126 mg). $R_F$ value = 0.45 (trichloromethane-methanol-acetic acid mixture, 80:10:5). Amino acid analysis shows the desired ratios.

Then peptide fragment III containing amino acids 12 to 15 (Ddz-Pro-His-Ile-Cys[Acm]) is formed. It is split off from the support material in the manner described above. The material is purified over silica gel using a trichloromethane-methanol gradient, and crystallized from methanol. M.P. = 170° C. The pure yield is 20%, and the amino acid analysis is in harmony with the theory.

Then peptide fragment IV (Ddz-Arg[Tos]-Lys[Z]-IleCys[StBu]-Gly-Lys[Z]-Asp[OBzl]), which includes the amino acids 16 to 22, is formed with a yield of 84%. Then 0.9 milliequivalents of the pure peptide fragment III is bound to the homogeneous peptide fragment IV (4.5 g, 0.21 milliequivalents per gram) which is present on the support material, operating in accordance with the dicyclohexylcarbodiimide/1-hydroxybenzotriazole (HOBt) method in dimethylformamide. Within three days, photometric observation of the reaction solution indicates that 73% of peptide fragment III has been incorporated. The remaining free amino groups of peptide fragment IV are blocked with 3-nitrophthalic acid anhydride (0.1 mole/1 in pyridine, action time 10 minutes), in order to suppress the formation of erroneous sequences. In this manner, peptide fragment IV (Ddz-Pro-His-Ile-Cys[Acm]]-Arg[Tos]-Lys[Z]-Ile-Cys[StBu]-Gly-Lys[Z]-Asp[OBzl]) is obtained on the support and contains amino acids 16 to 22; the yield is 24%.

Lastly, the final condensation of 126 mg of peptide fragment V is performed, which includes amino acids 1 to 11, on peptide fragment VI on the support material, by means of the dicyclohexylcarbodiimide/1-hydroxybenzotriazole(HOBt) method in dimethylformamide, using a three-fold excess of the peptide fragment in solution. After five days, the complete reaction of peptide fragment V can be verified, the completely protected MCD peptide being obtained with a yield of 32%.

The fully protected MCD peptide is then split off from the support material by ammonolysis, using a saturated solution of ammonia in dioxane as the reagent. The cleavage is continued for four and a half days at room temperature while supervising the reaction photometrically. Then the cleavage solution is processed in a conventional manner in order to purify the fully protected MCD peptide. In the thin layer chromatography the purified material shows a main spot at $R_F$ 0.4 (mixture of chloroform, methanol and acetic acid 85:10:5) or of 0.45 (mixture of sec.-butanol, acetic acid and water 4:1:1).

In the next step, the protective groups are split off with trifluoromethanesulfonic acid. To this end the trifluoromethanesulfonic acid is added to the well-dried peptide, dimethylsulfide is used as the cation scavenger and the mixture is stirred with the exclusion of moisture for one hour at room temperature, after which the peptide is precipitated with ether, transformed to the acetate form, and purified. In this treatment, the benzyloxycarbonyl protective group (Z) and the tosyl protective group (Tos) are split off, while the tert.-butylmercapto protective group (StBu) and the acetamidomethyl protective group (Acm), which are the groups protecting the sulfur groups, are not attacked.

For the formation of the disulfide bridges $Cys^5$-$Cys^{19}$ or $Cys^3$-$Cys^{15}$, the procedure followed is that described by J. van Rietschoten et al. (Europ. J. Biochem. 56 [1975] 34 to 40), P. Hartter, U. Weber, Hoppe Seyler's Z. Physiol. Chem. 356 [1975] 693, and P. Sieber et al., Helv. Chim. Acta 60, 4 [1977] 36). The material is purified in a conventional manner and in various analyses it is shown to be equal to the corresponding natural product, and in a pharmacological test it behaves similarly thereto. For example, in thin layer chromatography on cellulose plates, in paper electrophoresis, in disk electrophoresis on plates and on SDS gels, and in high-pressure liquid chromatography it acts in the same manner as the corresponding MCD natural product. The amino acid analysis also corresponds to that of the natural product.

The pharmacological tests show that the MCD peptide synthetically prepared in accordance with the invention has 26% of the activity of the natural product with regard to the release of histamine. By purifying the MCD peptide by high pressure liquid chromatography, a purified synthesis product can be obtained which has 35% of the pharmacological activity of the natural product.

It will be understood that the specification and examples are illustrative, but not limitative of the present invention and that other embodiments within the spirit and scope of the invention will suggest themselves to those skilled in the art.

What is claimed is:

1. Method for the preparation of a polypeptide comprising the steps of (a) condensing a carrier material consisting of less than 0.5% cross-linked polystyrene gel and including bromacetyl phenyl groups whereby the gel is activated with a member selected from the group consisting of peptide fragments composed of at least 3 amino-acids, isoleucine, leucine, valine, protective group bearing cysteine and protective group bearing lysine, each member having an N-terminal of alpha-alpha-dimethyl-3,5-dimethoxy benzyloxycarbonyl to protect the N-terminal and provide a means for photometric following of the reaction;

(b) condensing the resulting carrier bound member with one or more amino-acids or peptide fragments to form a peptide moiety;

(c) splitting off the peptide moiety;

(d) separating the peptide from contaminating by-products;

(e) introducing an N-terminal of alpha-alpha-dimethyl-3,5-dimethoxybenzyloxycarbonyl into the peptide moiety; and (f) condensing the product of step (e) again with the carrier material of step (a) and repeating steps (b) to (f) until the peptide moiety, formed on the carrier material, is equivalent to the desired end product polypeptide, and thereafter splitting off the peptide moiety and isolating the desired end product polypeptide thus freed.

2. Method as claimed in claim 1 wherein several different peptide fragments of the desired polypeptide are prepared independently of one another and split off from the support material, and then two peptide fragments adjacent one another in the desired sequence are condensed with one another, one of which is bound to the support material.

3. Method as claimed in claim 1 wherein said polypeptide is mast cell degranulating peptide MCD.

4. Method as claimed in claim 1 for preparing MCD comprising first forming separately the peptide fragments I (Ddz-Ile-Lys[Z]-Cys[Acm]-Asn-Cys[StBu]-Lys[Z]-Arg[Tos]), II (Ddz-His[Bos]-val-Ile-Lys[Z]), III (Ddz-Pro-His-Ile-Cys[Acm]) and IV (Ddz-Arg[Tos]-Lys[Z]-Ile-Cys[StBu]-Gly-Lys[Z]-Asp[OBzl]), joining the fragments I and II, and III and IV, respectively to the fragments V (Ddz-Ile-Lys[Z]-Cys[Acm]-Asn-Cys[StBu]-Lys[Z]-Ars[Tos]-His[Boc]-Val-Ile-Lys[Z]) and VI (Ddz-Pro-His-Ile-Cys[Acm]-Ars[Tos]-Lys[Z]-Ile-Cys[StBu]-Gly-Lys[Z]-Asp[OBzl]) and then combining fragments V and VI to form the protected peptide VII bound to the carrier material (Ddz-Ile-Lys[Z]-Cys[Acm]-Asn-Cys[StBu]-Lys[Z]-Arg[Tos]-His[Boc]-Val-Ile-Lys[Z]-Pro-His-Ile-Cys[Acm]-Arg[Tos]-Lys[Z]-Ile-Cys[StBu]-Gly-Lys[Z]-Asp[ABzl]), splitting off peptide VII from the support and splitting off the protective groups, forming the disulfide bridges $Cys^5$-$Cys^{19}$ and $Cys^3$-$Cys^{15}$.

* * * * *